United States Patent
Hayashi

(10) Patent No.: US 10,259,940 B2
(45) Date of Patent: Apr. 16, 2019

(54) THERMOPLASTIC ELASTOMER COMPOSITION, THERMOPLASTIC ELASTOMER, AND METHOD FOR PRODUCING THERMOPLASTIC ELASTOMER

(71) Applicant: ADVANCED SOFTMATERIALS INC., Kashiwa-shi, Chiba (JP)

(72) Inventor: Yuki Hayashi, Kashiwa (JP)

(73) Assignee: ADVANCED SOFTMATERIALS INC., Kashiwa-shi, Chiba (JP)

( * ) Notice: Subject to any disclaimer, the term of this patent is extended or adjusted under 35 U.S.C. 154(b) by 0 days.

(21) Appl. No.: 15/542,904

(22) PCT Filed: Jan. 12, 2016

(86) PCT No.: PCT/JP2016/050620
§ 371 (c)(1),
(2) Date: Jul. 11, 2017

(87) PCT Pub. No.: WO2016/114243
PCT Pub. Date: Jul. 21, 2016

(65) Prior Publication Data
US 2017/0369704 A1    Dec. 28, 2017

(30) Foreign Application Priority Data
Jan. 13, 2015 (JP) ................................ 2015-004545

(51) Int. Cl.
| | |
|---|---|
| C08L 75/08 | (2006.01) |
| C08G 18/48 | (2006.01) |
| C08G 18/42 | (2006.01) |
| C08G 18/44 | (2006.01) |
| C08L 71/02 | (2006.01) |
| C08L 75/04 | (2006.01) |
| A61L 29/00 | (2006.01) |

(52) U.S. Cl.
CPC .............. *C08L 75/08* (2013.01); *C08G 18/42* (2013.01); *C08G 18/44* (2013.01); *C08G 18/48* (2013.01); *C08L 71/02* (2013.01); *C08L 75/04* (2013.01); *A61L 29/00* (2013.01)

(58) Field of Classification Search
CPC ........ C08G 18/42; C08G 18/44; C08G 18/48; C08L 71/02; C08L 75/04; C08L 75/08; A61L 29/00
See application file for complete search history.

(56) References Cited

U.S. PATENT DOCUMENTS

| | | |
|---|---|---|
| 2009/0175921 A1 | 7/2009 | Gunatillake et al. |
| 2011/0124823 A1 | 5/2011 | Hayashi et al. |
| 2011/0287102 A1 | 11/2011 | Gunatillake et al. |
| 2012/0316278 A1 | 12/2012 | Inoue et al. |
| 2014/0296450 A1 | 10/2014 | Hayashi et al. |
| 2015/0105530 A1 | 4/2015 | Gunatillake et al. |
| 2017/0165530 A1* | 6/2017 | Tachibana .......... A63B 37/0096 |

FOREIGN PATENT DOCUMENTS

| | | |
|---|---|---|
| JP | 2009-508598 A | 3/2009 |
| JP | 2011-241401 A | 12/2011 |
| WO | 2010/024431 A1 | 3/2010 |
| WO | 2011/105532 A1 | 9/2011 |
| WO | 2011/108514 A1 | 9/2011 |
| WO | 2011/108515 A1 | 9/2011 |
| WO | 2012/165401 A1 | 12/2012 |
| WO | 2013/099842 A1 | 4/2013 |
| WO | 2015/174187 A1 | 11/2015 |
| WO | WO-2015174187 A1 * | 11/2015 ................ C08J 5/18 |

OTHER PUBLICATIONS

WO2015174187 English Machine Translation made Jul. 17, 2018. (Year: 2018).*
International Preliminary Report on Patentability and Written Opinion dated Jul. 27, 2017, in corresponding International Patent Application No. PCT/JP2016/050620, filed Jan. 12, 2016, 7 pages.
International Search Report dated Mar. 15, 2016, in corresponding International Patent Application No. PCT/JP2016/050620, filed Jan. 12, 2016, 2 pages.

* cited by examiner

*Primary Examiner* — Christopher M Rodd
(74) *Attorney, Agent, or Firm* — Christensen O'Connor Johnson Kindness PLLC

(57) ABSTRACT

The present invention provides a thermoplastic elastomer (TPE), in particular a polyurethane-based thermoplastic elastomer (TPU), that has exceptional elongation, strength, and wear resistance, and in particular has exceptional wear resistance. The present invention provides: a thermoplastic elastomer composition containing A) a thermoplastic urethane elastomer composition having A1) at least one polyol selected from the group consisting of polyether polyols, polyesterpolyols, and polycarbonate polyols, A2) a diisocyanate, and A3) a chain extender, and B) polyrotaxane formed by arranging blocking groups, at both ends of pseudo-polyrotaxane formed by inclusion of the openings of cyclic molecules in a shape skewered by linear molecules, so that the cyclic molecules are not eliminated; and a thermoplastic elastomer derived from this composition.

7 Claims, No Drawings

THERMOPLASTIC ELASTOMER COMPOSITION, THERMOPLASTIC ELASTOMER, AND METHOD FOR PRODUCING THERMOPLASTIC ELASTOMER

TECHNICAL FIELD

The present invention relates to a composition used for a thermoplastic elastomer comprising a A) thermoplastic urethane elastomer composition; and a B) polyrotaxane; a thermoplastic elastomer derived from the composition, and a method for producing the thermoplastic elastomer.

BACKGROUND ART

A thermoplastic elastomer (TPE) has both of excellent processing characteristics of plastic and characteristics of an elastomer. Specifically, in the TPEs, there are those which form a copolymer by chemical bonding of a hard segment and a soft segment in a polymer and those which blend a hard polymer and a soft polymer to form a sea-island structure. Since the hard segment plays a role of a pseudo-crosslinking point (being not a covalent bond), elasticity like rubber is exhibited. The hard segment is melt at high temperature to lose the function of the crosslinking point so that it undergoes plastic deformation and thus can flow.

Examples of the TPEs include olefin-based, styrene-based, polyester-based, polyurethane-based, polyamide-based, and fluorine-based TPEs, according to the type of a polymer that constitutes the TPE.

Of them, a polyurethane-based elastomer (TPU) is excellent in flexibility, bending resistance, and mechanical strength, and thus the TPU is used for various use applications for automobiles, civil engineering and construction, electric and electronic equipment, and sports equipment.

In order to improve the physical property of the TPU, for example, elongation, a relatively low-molecular weight phthalate ester-based plasticizer is used. However, when the plasticizer is used, problems of decreased strength of the TPU, bleeding out of the plasticizer due to the long-term use thereof, decreased wear resistance, and the like occur and thus, depending on the use application, the use of the plasticizer affects adversely in some cases.

A polyrotaxane has properties that, when a cyclic molecule constituting the polyrotaxane moves on the linear molecule, viscoelasticity, low compression permanent strain, and the like occur in a crosslinked body of polyrotaxanes, a crosslinked body of a polyrotaxane and a polymer other than the polyrotaxane, and the like. For this reason, the polyrotaxane is expected to be applied to various use applications, and thus, research and development thereof have been actively conducted.

For example, Patent Document 1 discloses a photocross-linkable polyrotaxane, wherein a cyclic molecule of a polyrotaxane has a photopolymerizable group at side chain terminals of a lactone or carbonate polymer, a cured product formed by using the polyrotaxane, and the like. In addition, it is disclosed that the cured product has properties such as scratch resistance, folding resistance, and low hysteresis loss.

However, the cured product disclosed in Patent Document 1 is a thermosetting, and thus Patent Document 1 does not disclose nor suggest a thermoplastic polymer, in particular, a thermoplastic elastomer.

PRIOR ART DOCUMENT

Patent Document

Patent Document 1: WO2011/105532

DISCLOSURE OF THE INVENTION

Problems to be Solved by the Invention

An object of the present invention is to provide a thermoplastic elastomer (TPE), in particular a polyurethane-based thermoplastic elastomer (TPU) having excellent elongation, strength, and wear resistance, in particular, excellent wear resistance.

Further, an object of the present invention is, in addition to the above object, to provide a composition, which forms the thermoplastic elastomer (TPE), in particular the polyurethane-based thermoplastic elastomer (TPU).

More, an object of the present invention is, in addition to, or other than the above object, to provide a method for producing the thermoplastic elastomer (TPE), in particular the polyurethane-based thermoplastic elastomer (TPU).

Means for Solving Problems

The present inventor has found the following inventions:
<1> A composition used for a thermoplastic elastomer comprising A) a thermoplastic urethane elastomer composition comprising A1) at least one polyol selected from the group consisting of polyether polyols, polyester polyols, and polycarbonate polyols, A2) a diisocyanate, and A3) a chain extender; and B) a polyrotaxane comprising a pseudopolyrotaxane, which has a linear molecule and a cyclic molecule (s) in which the linear molecule is included in a cavity (cavities) of the cyclic molecule(s) in a skewered manner, and capping groups, each of which locates at each end of the pseudopolyrotaxane in order to prevent the dissociation of the cyclic molecule(s).

<2> In the above item <1>, the cyclic molecule in the B) polyrotaxane may comprise B1) a hydrophobic modifying group; and B2) at least one functional group selected from the group consisting of —OH, —$NH_2$ and —SH.

<3> In the above item <2>, the B1) hydrophobic modifying group may be a hydrophobic modifying group derived from caprolactone, and the B2) functional group may be —OH.

<4> In any one of the above items <1> to <3>, the B) polyrotaxane may be 0.10 to 10.0 parts by weight, preferably 0.2 to 6.0 parts by weight, more preferably 0.3 to 3.0 parts by weight, based on 100 parts by weight of the A) thermoplastic urethane elastomer composition.

<5> A thermoplastic elastomer derived from the composition used for a thermoplastic elastomer according to any one of the above items <1> to <4>.

<6> In the above item <5>, a ratio X/Y of a first Taber abrasion amount X, which is a measurement value of the thermoplastic elastomer in a Taber abrasion test T, to a second Taber abrasion amount Y, which is a measurement value of a comparative thermoplastic elastomer formed by excluding the B) component from the thermoplastic elastomer in the Taber abrasion test T, may be 0.85 or less, preferably 0.80 or less, more preferably from 0.05 to 0.75, most preferably from 0.10 to 0.65.

<7> A method for producing a thermoplastic elastomer comprising the steps of:

1) preparing a A) thermoplastic urethane elastomer composition comprising A1) at least one polyol selected from the group consisting of polyether polyols, polyester polyols, and polycarbonate polyols, A2) a diisocyanate, and A3) a chain extender;

2) preparing a B) polyrotaxane comprising a pseudopolyrotaxane, which has a linear molecule and a cyclic molecule (s) in which the linear molecule is included in a cavity (cavities) of the cyclic molecule (s) in a skewered manner, and capping groups, each of which locates at each end of the pseudopolyrotaxane in order to prevent the dissociation of the cyclic molecule(s);

3) mixing the A) thermoplastic urethane elastomer composition and the B) polyrotaxane, to obtain a composition used for a thermoplastic elastomer; and 4) heating and forming the composition used for a thermoplastic elastomer, followed by cooling, to obtain the thermoplastic elastomer.

<8> In the above item <7>, the cyclic molecule in the B) polyrotaxane may comprise B1) a hydrophobic modifying group; and B2) at least one functional group selected from the group consisting of —OH, —NH$_2$ and —SH.

<9> In the above item <8>, the B1) hydrophobic modifying group may be a hydrophobic modifying group derived from caprolactone, and the B2) functional group may be —OH.

<10> In any one of the above items <7> to <9>, the B) polyrotaxane may be 0.10 to 10.0 parts by weight, preferably 0.2 to 6.0 parts by weight, more preferably 0.3 to 3.0 parts by weight, based on 100 parts by weight of the A) thermoplastic urethane elastomer composition.

<11> In any one of the above items <7> to <10>, a ratio X/Y of a first Taber abrasion amount X, which is a measurement value of the thermoplastic elastomer in a Taber abrasion test T, to a second Taber abrasion amount Y, which is a measurement value of a comparative thermoplastic elastomer formed by excluding the B) component from the thermoplastic elastomer in the Taber abrasion test T, may be 0.85 or less, preferably 0.80 or less, more preferably from 0.05 to 0.75, most preferably from 0.10 to 0.65.

Effects of the Invention

The present invention can provide the present invention is to provide a thermoplastic elastomer (TPE), in particular a polyurethane-based thermoplastic elastomer (TPU) having excellent elongation, strength, and wear resistance, in particular, excellent wear resistance.

Further, in addition to the above effect, the present invention can provide a composition, which forms the thermoplastic elastomer (TPE), in particular the polyurethane-based thermoplastic elastomer (TPU).

More, in addition to, or other than the above effect, the present invention can provide a method for producing the thermoplastic elastomer (TPE), in particular the polyurethane-based thermoplastic elastomer (TPU).

EMBODIMENTS FOR CARRYING OUT THE INVENTION

The present invention will be described in detail hereinafter.

The present application discloses a composition used for a thermoplastic elastomer comprising a A) composition used for a thermoplastic urethane elastomer; and a B) polyrotaxane; a thermoplastic elastomer derived from the composition used for a thermoplastic elastomer, and a method for producing the thermoplastic elastomer. Hereinafter, these will be described.

<A Composition Used for a Thermoplastic Elastomer>

The present application discloses a composition used for a thermoplastic elastomer comprising A) a thermoplastic urethane elastomer composition comprising A1) at least one polyol selected from the group consisting of polyether polyols, polyester polyols, and polycarbonate polyols, A2) a diisocyanate, and A3) a chain extender; and B) a polyrotaxane comprising a pseudopolyrotaxane, which has a linear molecule and a cyclic molecule (s) in which the linear molecule is included in a cavity (cavities) of the cyclic molecule(s) in a skewered manner, and capping groups, each of which locates at each end of the pseudopolyrotaxane in order to prevent the dissociation of the cyclic molecule(s).

Hereinafter, these are described in detail, in order of "A) a thermoplastic urethane elastomer composition", and "B) a polyrotaxane".

<A) Thermoplastic Urethane Elastomer Composition>

In the composition used for a thermoplastic elastomer according to the present application, the A) thermoplastic urethane elastomer composition comprises A1) at least one polyol selected from the group consisting of polyether polyols, polyester polyols, and polycarbonate polyols, A2) a diisocyanate, and A3) a chain extender.

The thermoplastic urethane elastomer composition may be a commercially available product or may be prepared by an existing method.

Hereinafter, the A1) polyol, the A2) diisocyanate, and the A3) chain extender will be described in detail.

<<A1) Polyol>>

The A1) polyol is at least one selected from the group consisting of polyether polyols, polyester polyols, and polycarbonate polyols.

The number average molecular weight of the A1) polyol may be from 500 to 5,000, preferably from 600 to 4,000, more preferably from 700 to 3,000.

Examples of the polyether polyols among polyol components may include, but are not limited to, polypropylene glycol, polyethylene glycol, polytetramethylene glycol, aromatic polyether ether ketone and copolymers thereof, and the like.

Further, examples of the polyester polyols among polyol components may include, but are not limited to, polycaprolactone glycol, polylactic acid, polyethylene adipate glycol, polybutylene adipate glycol, and the like.

Furthermore, examples of the polycarbonate polyols among polyol components may include, but are not limited to, polycarbonate diols formed from a polycondensate obtained by ester exchange reaction between ethylene carbonate and diol (examples of the diol component include ethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 2-ethyl-1,6-hexandiol, 2-methyl-1,3-propanediol, 3-methyl-1,5-pentanediol and 2,4-diethyl-1,5-pentanediol, 2,2-dimethyl-1,3-propanediol, 1,4-dihydroxyethylclohexane, isosorbide, spiroglycol, 2,5-bis(hydroxymethyl) tetrahydrofuran, 4,4'-isopropylidene dicyclohexanol, m- or p-xylylene glycol, bisphenol A), and the like.

The polyol may be preferably polypropylene glycol, polytetramethylene glycol, polycaprolactone glycol, polyethylene adipate glycol, polybutylene adipate glycol, or polycarbonate diol, more preferably polypropylene glycol, polytetramethylene glycol, or polycaprolactone glycol.

<<A2) Diisocyanate>>

Examples of the A2) diisocyanate may include, but are not limited to, ethylene diisocyanate, tetramethylenediisocyanate, hexamethylenediisocyanate (HDI), dodecamethylenediisocyanate, 2,2,4-trimethylhexamethylene diisocyanate, lysine diisocyanate, 2,6-diisocyanato methylcaproate, bis(2-isocyanatoethyl)fumarate, bis(2-isocyanatoethyl)carbonate, 2-isocyanatoethyl-2,6-diisocyanatohexanoate, isophorone diisocyanate (IPDI), dicyclohexylmethane-4,4'-diisocyanate (hydrogenated MDI), cyclohexylene diisocyanate, methylcyclohexylene diisocyanate (hydrogenated TDI), bis(2-isocyanatoethyl)-4-cyclohexene, 1,3- and/or 1,4-phenylene diisocyanate, 2,4- and/or 2,6-tolylenediisocyanate (TDI), crude TDI, 2,4'- and/or 4,4'-diphenylmethane diisocyanate (MDI), 4,4'-diisocyanato biphenyl, 3,3'-dimethyl-4,4'-diisocyanato biphenyl, 3,3'-dimethyl-4,4'-diisocyanato diphenylmethane, crude MDI, 1,5-naphthalene diisocyanate, m- and/or p-xylylene diisocyanate (XDI), α,α,α',α'-tetramethyl xylylene diisocyanate (TMXDI), and the like.

The A2) diisocyanate may be preferably 2,4- and/or 2,6-tolylenediisocyanate (TDI), crude TDI, 2,4'- and/or 4,4'-diphenylmethane diisocyanate (MDI), crude MDI, hexamethylene diisocyanate (HDI), 2-isocyanatoethyl-2,6-diisocyanatohexanoate, isophorone diisocyanate (IPDI), dicyclohexylmethane-4,4'-diisocyanate (hydrogenated MDI), cyclohexylene diisocyanate, or methylcyclohexylene diisocyanate (hydrogenated TDI), more preferably 2,4- and/or 2,6-tolylenediisocyanate (TDI), crude TDI, 2,4'- and/or 4,4'-diphenylmethane diisocyanate (MDI), crude MDI, or hexamethylene diisocyanate (HDI).

<<A3) Chain Extender>>

As the A3) chain extender, a low-molecular weight diol or diamine having a number average molecular weight of 50 to 400, preferably 80 to 350, more preferably 100 to 300 can be used.

Specific examples of the diol may include, but are not limited to, aliphatic diols such as ethylene glycol, diethylene glycol, 1,3-propanediol, 1,4-butanediol, 1,5-pentanediol, 1,6-hexanediol, propylene glycol, neopentyl glycol, 3-methyl 1,5-pentanediol, 2,2-diethyl-1,3-propanediol, 1,2-, 1,3- or 2,3-butanediol, a diol reaction product of adipic acid and 1,4-butanediol, and a diol reaction product of adipic acid and 1,6-hexanediol; alicyclic diols such as 1,4-bis(hydroxymethyl)cyclohexane; m- or p-xylylene glycol; aromatic diols such as an ethylene oxide or propylene oxide adduct of bisphenol A; and mixtures of two or more thereof, and the like.

Specific examples of diamine may include, but are not limited to, aromatic diamines such as 4,4'-diaminodiphenylmethane, 4,4'-diaminodiphenyl ether, 4,4'-bis(4-aminophenoxy)biphenyl, 4,4'-bis(3-aminophenoxy)biphenyl, 1,4'-bis(4-aminophenoxy)benzene, 1,3'-bis(4-aminophenoxy)benzene, 1,3-bis(3-aminophenoxy)benzene, o-phenylenediamine, m-phenylenediamine, p-phenylenediamine, 3,4'-diaminodiphenyl ether, 4,4'-diaminodiphenyl sulfone, 3,4-diaminodiphenyl sulfone, 3,3'-diaminodiphenyl sulfone, 4,4'-methylene-bis(2-chloroaniline), 3,3'-dimethyl-4,4'-diaminobiphenyl, 4,4'-diaminodiphenyl sulfide, 2,6'-diaminotoluene, 2,4-diaminochlorobenzene, 1,2-diaminoanthraquinone, 1,4-diaminoanthraquinone, 3,3'-diaminobenzophenone, 3,4-diaminobenzophenone, 4,4'-diaminobenzophenone, 4,4'-diaminobibenzyl, R(+)-2,2'-diamino-1,1'-binaphthalene, S(+)-2,2'-diamino-1,1'-binaphthalene, 1,n-bis(4-aminophenoxy)alkane (n is 3 to 10) such as 1,3-bis(4-aminophenoxy)alkane, 1,4-bis(4-aminophenoxy)alkane, or 1,5-bis(4-aminophenoxy)alkane, 1,2-bis[2-(4-aminophenoxy)ethoxy]ethane, 9,9-bis(4-aminophenyl) fluorene, and 4,4'-diaminobenzanilide; aliphatic diamines such as 1,2-diaminomethane, 1,4-diaminobutane, tetramethylenediamine, 1,5-diaminopentane, 1,6-diaminohexane, 1,8-diaminooctane, 1,10-diaminododecane, and 1,11-diaminoundecane; and mixtures of two or more kinds thereof, and the like.

The A3) chain extender may be preferably ethylene glycol, 1,4-butanediol, 1,6-hexanediol, neopentyl glycol, ethylene oxide or propylene oxide adduct of bisphenol A, 1,2-diaminomethane, 1,4-diaminobutane, and tetramethylene diamine.

The A) thermoplastic urethane elastomer composition may comprise components other than the components A1) to A3). Examples of the above-described components may include, but are not limited to, particles such as silica particles, alumina particles, styrene particles, styrene-butadiene particles, or carbon black; ultraviolet absorbing agents; antistatic agents; flame retardants; delustering agents, and the like.

<B) Polyrotaxane>

The B) polyrotaxane is comprised of a pseudopolyrotaxane, which has a linear molecule and a cyclic molecule (s) in which the linear molecule is included in a cavity (cavities) of the cyclic molecule(s) in a skewered manner, and capping groups, each of which locates at each end of the pseudopolyrotaxane in order to prevent the dissociation of the cyclic molecule (s).

An amount of the B) polyrotaxane may be 0.10 to 10.0 parts by weight, preferably 0.2 to 6.0 parts by weight, more preferably 0.3 to 3.0 parts by weight, based on 100 parts by weight of the A) thermoplastic urethane elastomer composition.

<<B-1. Cyclic Molecule>>

The cyclic molecule of the B) polyrotaxane is not limited as long as the cyclic molecule may be cyclic, and may have a cavity, and a linear molecule is included in the cavity (cavities) of the cyclic molecules in a skewered manner.

The cyclic molecule may have B1) a hydrophobic modifying group; and B2) at least one functional group selected from the group consisting of —OH, —NH$_2$ and —SH.

Examples of the B1) hydrophobic modifying group may include, but are not limited to, groups having a hydrophobic group such as an acetyl group, a butyl ester group, a hexyl ester group, an octadecyl ester group, a polycaprolactone group, a poly(δ-valerolactone) group, a polylactic acid group, a polyalkylene carbonate group, a polypropylene glycol group, a polytetramethylene glycol group, a polymethyl acrylate group, and a polyethylhexyl acrylate group, and the like. Among them, a polycaprolactone group and a polyalkylene carbonate group are preferable.

The cyclic molecule may comprise B2) at least one functional group selected from the group consisting of —OH, —NH$_2$, and —SH in addition to the "B1) hydrophobic modifying group".

The functional group may be directly bonded to the cyclic molecule or may be bonded to the cyclic molecule via the "B1) hydrophobic modifying group".

The B1) hydrophobic modifying group may be a hydrophobic modifying group derived from caprolactone, and the B2) functional group may be —OH.

The cyclic molecule may be, for example, selected from the group consisting of α-cyclodextrin, β-cyclodextrin and γ-cyclodextrin.

The above-described B1) hydrophobic modifying group; and/or the B2) functional group may be obtained by substituting with a part of —OH groups in α-cyclodextrin and the like.

<<B-2. Linear Molecule>>

The linear molecule of the B) polyrotaxane is not limited as long as the linear molecule may be included in a cavity (cavities) of the cyclic molecule(s) in a skewered manner.

For example, the linear molecule may include polyvinyl alcohol, polyvinylpyrrolidone, poly(meth)acrylic acid, cellulose-based resins (carboxymethylcellulose, hydroxyethylcellulose, hydroxypropylcellulose and the like), polyacrylamide, polyethylene oxide, polyethylene glycol, polypropylene glycol, polyvinyl acetal-based resins, polyvinyl methyl ether, polyamine, polyethyleneimine, casein, gelatin, starch and the like and/or copolymers thereof, polyolefin-based resins such as polyethylene, polypropylene, and copolymer resins with other olefinic monomers, polyester resins, polyvinyl chloride resins, polystyrene-based resins such as polystyrene, acrylonitrile-styrene copolymer resin and the like, acrylic resins such as polymethyl methacrylate, copolymer of (meth)acrylate, acrylonitrile-methyl acrylate copolymer resin and the like, polycarbonate resins, polyurethane resins, vinyl chloride-vinyl acetate copolymer resin, polyvinylbutyral resin and the like; and derivatives and modifications thereof, polyisobutylene, polytetrahydrofuran, polyaniline, acrylonitrile-butadiene-styrene copolymer (ABS resin), polyamides such as nylon and the like, polyimides, polydienes such as polyisoprene, polybutadiene and the like, polysiloxanes such as polydimethylsiloxane and the like, polysulfones, polyimines, polyacetic anhydrides, polyureas, polysulfides, polyphosphazenes, polyketones, polyphenylenes, polyhaloolefins, and derivatives thereof. For example, the linear molecule may be selected from the group consisting of polyethylene glycol, polyisoprene, polyisobutylene, polybutadiene, polypropylene glycol, polytetrahydrofuran, polydimethylsiloxane, polyethylene, polypropylene, polyvinyl alcohol and polyvinyl methyl ether. In particular, the linear molecule may be polyethylene glycol.

A weight average molecular weight of the linear molecule may be 1,000 or more, preferably 3,000 to 100,000, more preferably 6,000 to 50,000.

In the B. polyrotaxane, the combination of (cyclic molecule, linear molecule) may be (one derived from α-cyclodextrin, one derived from polyethylene glycol).

<<B-3. Capping Group>>

The capping group of the B. polyrotaxane is not limited, as long as the group is located at both ends of a pseudopolyrotaxane, and the group has a function of preventing dissociation of a cyclic molecule(s) from a linear molecule.

For example, the capping group may be selected from the group consisting of dinitrophenyl groups; cyclodextrins; adamantane groups; trityl groups; fluoresceins; silsequioxanes; pyrenes; substituted benzenes (example of the substituent may, include, but are not limited to, alkyl, alkyloxy, hydroxy, halogen, cyano, sulfonyl, carboxyl, amino, phenyl and the like. The substituent may be single or plural.); polycyclic aromatics which may be substituted (examples of the substituent may include, but are not limited to, those described above. The substituent may be single or plural.); and steroids. Preferably, the capping group may be selected from the group consisting of dinitrophenyl groups; cyclodextrins; adamantane groups; trityl groups; fluoresceins; silsequioxanes; and pyrenes, more preferably adamantane groups or cyclodextrins.

<<Other Components in the Composition Used for a Thermoplastic Elastomer>>

The composition used for a thermoplastic elastomer according to the present application may contain "other components" in addition to the A and B components.

Examples of the other components may include, but are not limited to, conductive agents such as carbon black, carbon nanotube, graphite, barium titanate, $TiO_2$, $ZnO$, and $SnO_2$; antistatic agents such as polyoxyethylene (18) octyl phenyl ether, polyoxyethylene sorbitan trioleate, polyoxyethylene(10) dodecyl ether, alkylsulfonic acid salt, tetraalkylbenzylammonium salt, and glycerin fatty acid ester; UV absorbing agents such as 2-ethylhexyl p-dimethylaminobenzoate, 2-ethylhexyl salicylate, 2,4-dihydroxybenzophenone, 2-hydroxy-4-n-octylbenzophenone, 2-(2'-hydroxy-5'-t-butylphenyl)benzotriazole, 2-ethylhexyl p-methoxycinnamate, isopropyl p-methoxycinnamate, and octyl methoxycinnamate; silver, zinc, copper compounds or complex or ions thereof; organosilicon compounds; antimicrobial agents such as organophosphorus compounds; antioxidants such as phenolic antioxidants, sulfur-based antioxidants, and phosphorus-based antioxidants; delustering agents such as acrylic particles, ethylene particles, styrene particles, styrene-butadiene particles, polyimide particles, polyurethane particles, silica, and alumina; flame retardants such as pentabromodiphenyl ether, decabromodiphenyl ether, tetrabromobisphenol A, hexabromocyclododecane, hexabromobenzene, triphenyl phosphate, aluminum hydroxide, and magnesium hydroxide; and pigments, and the like.

In addition, the composition used for a thermoplastic elastomer according to the present application may comprise a solvent depending on the use application.

<A Thermoplastic Elastomer Formed from the Above-described Composition Used for a Thermoplastic Elastomer, and a Method for Producing a Thermoplastic Elastomer>

The present application discloses a thermoplastic elastomer formed from the above-described composition used for a thermoplastic elastomer.

The thermoplastic elastomer can be produced by the following method from the above-described composition used for the thermoplastic elastomer:

The method comprises the steps of:

1) preparing a A) thermoplastic urethane elastomer composition comprising A1) at least one polyol selected from the group consisting of polyether polyols, polyester polyols, and polycarbonate polyols, A2) a diisocyanate, and A3) a chain extender;

2) preparing a B) polyrotaxane comprising a pseudopolyrotaxane, which has a linear molecule and a cyclic molecule (s) in which the linear molecule is included in a cavity (cavities) of the cyclic molecule (s) in a skewered manner, and capping groups, each of which locates at each end of the pseudopolyrotaxane in order to prevent the dissociation of the cyclic molecule(s);

3) mixing the A) thermoplastic urethane elastomer composition and the B) polyrotaxane, to obtain a composition used for a thermoplastic elastomer; and 4) heating and forming the composition used for a thermoplastic elastomer, followed by cooling, to obtain the thermoplastic elastomer.

<<Step 1)>>

The above-described step 1) can prepare a thermoplastic urethane elastomer composition with reference to the aforementioned thermoplastic urethane elastomer composition.

That is, the A1) polyol can be prepared by using a commercially available product and/or preparing a polyol.

Further, the A2) diisocyanate can be prepared by using a commercially available product and/or preparing a diisocyanate.

Moreover, the A3) chain extender can be prepared by using a commercially available product and/or preparing a chain extender.

The thermoplastic urethane elastomer composition can be produced, for example by reacting the A1) polyol, the A2) diisocyanate, and the A3) chain extender. As this method, there are generally known a one-shot method of mixing components at once and then reacting them; a prepolymer method of reacting the A1) polyol and the A2) diisocyanate in advance and then reacting the A3) chain extender; and the like. A composition obtained by the reaction may be in the form of powder or pellet for the purpose of easily performing heat processing at the time of molding a component or a product.

Furthermore, when the thermoplastic urethane elastomer composition comprises components other that the above components A1) to A3), the thermoplastic urethane elastomer composition can be prepared by using commercially available products as the other components and/or preparing the other components.

<<Step 2)>>

The above step 2) is a step of preparing a polyrotaxane. In this step, the polyrotaxane can be prepared by a known method, for example, the method described in WO2010/024431.

When the cyclic molecule comprises the B1) hydrophobic modifying group; and B2) at least one functional group selected from the group consisting of —OH, —NH$_2$, and —SH, the polyrotaxane can be obtained by substituting the —OH group of the cyclic molecule in the polyrotaxane obtained by the above-described known method with the B1) hydrophobic modifying group and the B2) functional group (excluding —OH group).

For example, when the —OH group of the cyclic molecule is substituted with the B1) hydrophobic modifying group, although depending on compatibility with a monomer or compound for providing a hydrophobic modifying group, solubility in a solvent used in the reaction, easiness of substitution reaction, or the like, a part of the —OH group of the cyclic molecule is first substituted with another substituent (for example, a hydroxypropyl group, a hydroxybutyl group, an acetyl group, a butylcarbamoyl group, or the like) and then the remaining —OH group of the cyclic molecule or the —OH group on the other substituent may be substituted with the hydrophobic modifying group. As a specific example, in a case where the cyclic molecule is cyclodextrin, a part of the hydroxyl group of the cyclodextrin is substituted with a hydroxypropyl group, and then —OH of the cyclodextrin and —OH of the hydroxypropyl group are modified with a polycaprolactone group that is a hydrophobic modifying group by using ε-caprolactone. Herein, the substitution with the hydroxypropyl group enables the produced polyrotaxane to be compatible with ε-caprolactone and thus the reaction can easily proceed.

In addition, the B2) functional group may be further provided on the hydrophobic modifying group.

The condition at the time of substituting the —OH group of the cyclic molecule with the B1) hydrophobic modifying group may be normal temperature to 130° C. and normal pressure, depending on a polyrotaxane to be used, a linear molecule to be used, a capping group to be used, or the like.

Further, in a case where the —OH group of the cyclic molecule in the polyrotaxane is substituted with the B2) functional group other than the —OH group, the substitution can be performed by using an existing substitution method or reaction method. For example, a carboxylic group is provided to the —OH group and then the —NH$_2$ group is provided to the carboxylic group, so that the B2) functional group can be the —NH$_2$ group. The condition at this time may be normal temperature to 130° C. and normal pressure, depending on a polyrotaxane to be used, a linear molecule to be used, a capping group to be used, or the like.

Further, in a case where the B1) hydrophobic modifying group is first provided, the B2) functional group can be provided to the B1) hydrophobic modifying group. In the case, depending on the group of the B1) hydrophobic modifying group, for example, in a case where the B1) hydrophobic modifying group has the —OH group, similarly to the above-described case, the —OH group can be substituted with the B2) functional group other than the —OH group by using an existing substitution method or reaction method, and for example, a carboxylic group is provided to the —OH group and then the —NH$_2$ group is provided to the carboxylic group so that the B2) functional group can be the —NH$_2$ group.

<<Step 3)>>

The above step 3) is a step of mixing the A) thermoplastic urethane elastomer composition prepared in the step 1) and the B) polyrotaxane prepared in the step 2), to obtain a composition used for a thermoplastic elastomer.

A solvent may or may not be used in the mixing. When a solvent is used, the solvent may be removed after the mixing.

<<Step 4)>>

The above step 4) is a step of heating and forming the composition used for a thermoplastic elastomer obtained above, followed by cooling. The heating and forming can be performed by an existing method. Examples of the existing method may include, but are not limited to, injection molding, extrusion molding, inflation molding, blow molding, powder molding, calendar molding, and the like.

The step of heating and forming may be performed under the condition of a temperature of 120 to 200° C., preferably 140 to 180° C., and a pressure of normal pressure to 80 kgf/cm$^2$, preferably 20 to 70 kgf/cm$^2$, depending on the A) thermoplastic urethane elastomer composition to be used, the B) polyrotaxane to be used, a mixing ratio of these components, or the like.

In addition, depending on the A) thermoplastic urethane elastomer composition to be used, the B) polyrotaxane to be used, a mixing ratio of these components, or the like, the cooling step may be performed at room temperature to 60° C.

<Thermoplastic Elastomer>

The thermoplastic elastomer can be obtained from the aforementioned composition used for a thermoplastic elastomer by the above-described method or the like.

The thermoplastic elastomer according to the present application may have a desired elongation, a desired strength, and a desired wear resistance.

<Elongation and Tensile Strength>

<<Tensile Strength, and Elongation>>

These properties are measured by a tensile test according to JIS K 7311. A test sample is pulled, and a stress at breakage is regarded as a tensile strength. Further, the elongation is based on the following equation. In the equation, by pulling the test sample having $L_0$: a length before the test, the length of the test sample at breakage is designated as Lt.

$$\text{Elongation (\%)}=(Lt-L_0)/L_0\times 100.$$

The thermoplastic elastomer according to the present application may have 200 to 800% as a desired elongation.

Further, the thermoplastic elastomer according to the present application may have 20 to 60 MPa as a tensile strength.

<Wear Resistance>

The thermoplastic elastomer according to the present application may have a desired value of an abrasion amount in a Taber abrasion test to be specifically described below.

Herein, in the Taber abrasion test, measurement is performed on I) a thermoplastic elastomer "I" formed from the composition used for a thermoplastic elastomer according to the present application and II) a thermoplastic elastomer "II" formed from a composition only excluding the B) component from the composition used for a thermoplastic elastomer used in the above I), under the same conditions.

A ratio X/Y of the Taber abrasion amount X of the thermoplastic elastomer "I" to the Taber abrasion amount Y of the thermoplastic elastomer "II", is obtained, and the X/Y may be 0.85 or less, preferably 0.80 or less, more preferably 0.05 to 0.75, most preferably 0.10 to 0.65.

Furthermore, since the Taber abrasion tests are performed under the same conditions, there is no change in the ratio X/Y, but preferably, both of the Taber abrasion tests may be performed under the conditions that the thicknesses of samples are set to be the same, the abrasion rotation numbers are set to be the same, and the types of abrading wheels are set to be the same.

Since the thermoplastic elastomer of the present application has the above-described properties, the thermoplastic elastomer can be used in automobile interior and/or exterior and/or functional components; electrical and electronic components such as electrical insulating materials, mobile phones, keyboard sheets, and watch bands; mechanical and industrial components such as packings, rollers and/or cleaning blades and/or housings of OA equipment, sealing materials, binders of inorganic materials, ball joints, gears, dust covers, hoses, tubes, casters, belt conveyors, electric cables, and round belts; sports and leisure components such as ski boots, sports shoes, and goggles; caring and medical materials such as caring bed materials, medical gloves, and dialysis tubes; adhesives, synthetic leather, containers, building materials, furniture, and the like, but the use of the thermoplastic elastomer is not limited thereto.

The present invention will be illustrated more specifically by way of following Examples, but is not limited thereby.

EXAMPLES

<A. Preparation of Thermoplastic Urethane Elastomer Composition>

As the thermoplastic urethane elastomer composition, RESAMINE P-2383 (manufactured by Dainichiseika Color & Chemicals Mfg. Co., Ltd.) that is a commercially available polyether polyol TPU was used.

<B. Preparation of Polyrotaxane>

A polyrotaxane was prepared by the method described in WO2005/080469 or WO2010/024431. More specifically, a polyrotaxane modified with a hydroxypropyl group (HAPR) was prepared by the method described in Example 3 of WO2005/080469.

Furthermore, the $^1$H-NMR analysis of the polyrotaxane as synthesized hereinafter was determined by 400 MHz JEOL JNM-AL400 (manufactured by JEOL Ltd.).

The measurement of the molecular weight and the molecular weight distribution of the polyrotaxane were carried out by using TOSOH HLC-8220 GPC instrument. The measurement was carried out under the conditions: column: TSK guard column Super AW-H and TSKgel Super AWM-H (two columns are linked); elution solution: dimethylsulfoxide (DMSO)/0.01 M LiBr; column oven: 50° C.; flow rate: 0.5 ml/min; sample concentration of about 0.2 wt/vol %; injection amount: 20 µl; pre-treatment: filtration using a 0.2 µm filter; and the standard molecular weight: PEO. Infrared spectroscopy (IR) was determined by Nicolet 4700 (manufactured by Thermo Fisher Scientific K.K.).

<<Preparation of Polyrotaxane Having Caprolactone Group>>

A polyrotaxane having a caprolactone group was produced by the following method in order to obtain compatibility with the polyether polyol (TPU, RESAMINE P-2383 (manufactured by Dainichiseika Color & Chemicals Mfg. Co., Ltd.)).

Into a three-necked flask, 10 g of the polyrotaxane (HAPR) as obtained in the above step was added, and under a slow nitrogen flow, 45 g of ε-caprolactone was added thereto. After stirring the content homogeneously at 100° C. for 30 minutes by a mechanical stirrer, the reaction temperature was raised to 130° C., and then, 1.6 g of tin 2-ethylhexanoate diluted with ethyl acetate (50 wt % solution) was added thereto. The mixture was allowed to react for 5 hours, followed by removing a solvent, to obtain 55 g of a polyrotaxane having a polycaprolactone group (PR). GPC determined the weight average molecular weight Mw of PR: 580,000 and its molecular weight distribution Mw/Mn: 1.5.

<Production and Physical Property Evaluation>

Example 1

0.25 part by weight of PR obtained above with respect to 100 parts by weight of pellet of the polyether polyol (TPU, RESAMINE P-2383 (manufactured by Dainichiseika Color & Chemicals Mfg. Co., Ltd.)) was molded by a general screw type injection molding machine.

The zone temperature of the injection machine was adjusted to 160 to 180° C. to obtain a sheet-shaped thermoplastic elastomer having a thickness of 2.0 mm. Evaluation items described below were carried out by using the sheet-shaped thermoplastic elastomer. The results thereof are shown in Table 1.

Example 2 to Example 4

A sheet-shaped thermoplastic elastomer having a thickness of 2.0 mm was obtained in a manner similar to Example 1, except that the amount of PR was changed from 0.25 part by weight to 0.50 part by weight (Example 2), 0.75 part by weight (Example 3), or 1.0 part by weight (Example 4) in Example 1. Then, the same evaluation items as in Example 1 were evaluated. The results thereof are also shown in Table 1.

Comparative Example 1

A sheet-shaped substance having a thickness of 2.0 mm was obtained in a manner similar to Example 1, except that PR in Example 1 was excluded. Then, the same evaluation items as in Example 1 were evaluated. The results thereof are also shown in Table 1.

<<Viscosity>>

The viscosity at 190° C. was measured by using a B-type viscometer (DV-E, manufactured by Brookfield Engineering).

<<Hardness (JIS A)>>

The hardness was measured according to JIS K 7311 by using a type-A durometer.

<<Tensile Strength, Elongation, 10% Modulus, 50% Modulus, and 100% Modulus>>

As described above, measurement was conducted by a tensile test according to JIS K 7311. A test sample was pulled, and a stress at breakage was regarded as a tensile strength.

Further, the elongation was based on the following equation. In the equation, by pulling the test sample having $L_0$: a length before the test, the length of the test sample at breakage was designated as Lt.

Elongation (%)=$(Lt-L_0)/L_0 \times 100$

The stresses in elongation of 10%, 50%, and 100% were designated as 10% modulus, 50% modulus, and 100% modulus, respectively.

<<Tear Strength>>

The tear strength was measured according to JIS K 7311 by using a right angle tear test sample.

<<Taber Abrasion>>

The abrasion amount (mg) was measured by using a Taber abrasion tester under the condition according to JIS K 7311. Furthermore, the samples of Examples 1 to 4 and Comparative Example 1 were adjusted to have a thickness of 2.0 mm so as to be the same as each other. In addition, all of the abrasion rotation numbers in the Taber abrasion test and the types of the abrading wheel in Examples 1 to 4 and Comparative Example 1 were set to be the same.

Further, the abrasion amount in Examples 1 to 4 is designated as X (abrasion amounts in Examples 1 to 4 are designated as X1 to X4 respectively), the abrasion amount in Comparative Example 1 is designated as Y, and the results of calculating X/Y are shown in Table 1.

It is shown from Table 1 that the thermoplastic elastomers of Examples 1 to 4 have a desired elongation, a desired strength, and a desired Taber abrasion amount. In particular, it is found out that regarding the Taber abrasion amount, the value of X/Y is 0.64 or less and the thermoplastic elastomers of Examples 1 to 4 have desired wear resistance. It can be considered that by blending the polyrotaxane, followed by mixing and processing under an appropriate condition, the cyclic molecule of the polyrotaxane and TPU are partially bonded to each other, and that according to the partial bonding, the obtained polyrotaxane-containing TPU can uniformly distribute stress to be applied at the time of abrasion, and thus can provide excellent abrasion characteristics. It can be said that slightly increased strength and elongation corresponds to the effect of blending the polyrotaxane.

TABLE 1

Composition and properties of Examples 1 to 4 and Comparative Example 1

|  | Example 1 | Example 2 | Example 3 | Example 4 | Comparative Example 1 |
|---|---|---|---|---|---|
| Composition |  |  |  |  |  |
| RESAMINE P-2383 | 100 | 100 | 100 | 100 | 100 |
| Polyrotaxane | 0.25 | 0.50 | 0.75 | 1.0 | 0 |
| Properties |  |  |  |  |  |
| Viscosity (dPa · s) | 29300 | 30100 | 27800 | 32100 | 27700 |
| Hardness (JIS A) | 83 | 83 | 83 | 83 | 83 |
| 10% Modulus (MPa) | 1.2 | 1.2 | 1.3 | 1.3 | 1.2 |
| 50% | 4.0 | 4.0 | 4.0 | 4.0 | 4.0 |
| 100% | 5.0 | 5.0 | 5.0 | 5.0 | 5.1 |
| Tensile strength (MPa) | 24.4 | 25.9 | 25.1 | 24.8 | 21.4 |
| Elongation (%) | 470 | 477 | 477 | 468 | 458 |
| Tear strength (kN/m) | 71.2 | 72.9 | 72.3 | 74.5 | 71.1 |
| Taber abrasion (mg) | 17 | 16 | 18 | 17 | 28 |
| X/Y | 0.61 | 0.57 | 0.64 | 0.61 | — |

What is claimed is:

1. A composition used for a thermoplastic elastomer comprising:
    A) a thermoplastic urethane elastomer composition comprising A1) at least one polyol selected from the group consisting of polyether polyols, polyester polyols, and polycarbonate polyols, A2) a diisocyanate, and A3) a chain extender; and
    B) a polyrotaxane comprising a pseudopolyrotaxane, which has a linear molecule and a cyclic molecule(s) in which the linear molecule is included in a cavity (cavities) of the cyclic molecule(s) in a skewered manner, and capping groups, each of which locates at each end of the pseudopolyrotaxane in order to prevent the dissociation of the cyclic molecule(s).

2. The composition used for a thermoplastic elastomer according to claim 1, wherein the cyclic molecule in the B) polyrotaxane comprises:
    B1) a hydrophobic modifying group; and
    B2) at least one functional group selected from the group consisting of —OH, —NH2 and —SH.

3. The composition used for a thermoplastic elastomer according to claim 2, wherein the B1) hydrophobic modifying group is a hydrophobic modifying group derived from caprolactone and the B2) functional group is —OH.

4. The composition used for a thermoplastic elastomer according to claim 1, wherein the B) polyrotaxane is 0.10 to 10.0 parts by weight based on 100 parts by weight of the A) thermoplastic urethane elastomer composition.

5. A thermoplastic elastomer derived from the composition used for a thermoplastic elastomer according to claim 1, wherein the A) thermoplastic urethane elastomer composition and the B) polyrotaxane are partially bonded to each other.

6. The thermoplastic elastomer according to claim 5, wherein a ratio X/Y of a first Taber abrasion amount X, which is a measurement value of the thermoplastic elastomer in a Taber abrasion test T, to a second Taber abrasion amount Y, which is a measurement value of a comparative thermoplastic elastomer formed by excluding the B) component from the thermoplastic elastomer in the Taber abrasion test T, is 0.85 or less.

7. A method for producing a thermoplastic elastomer comprising the steps of:
   1) preparing a A) thermoplastic urethane elastomer composition comprising A1) at least one polyol selected from the group consisting of polyether polyols, polyester polyols, and polycarbonate polyols, A2) a diisocyanate, and A3) a chain extender;
   2) preparing a B) polyrotaxane comprising a pseudopolyrotaxane, which has a linear molecule and a cyclic molecule(s) in which the linear molecule is included in a cavity (cavities) of the cyclic molecule(s) in a skewered manner, and capping groups, each of which locates at each end of the pseudopolyrotaxane in order to prevent the dissociation of the cyclic molecule(s);
   3) mixing the A) thermoplastic urethane elastomer composition and the B) polyrotaxane, to obtain a composition used for a thermoplastic elastomer; and
   4) heating and forming the composition used for a thermoplastic elastomer, followed by cooling, to obtain the thermoplastic elastomer.

\* \* \* \* \*